(12) United States Patent
Rossi et al.

(10) Patent No.: US 9,181,584 B2
(45) Date of Patent: Nov. 10, 2015

(54) METHODS FOR PRODUCING INTERFERING RNA MOLECULES IN MAMMALIAN CELLS AND THERAPEUTIC USES FOR SUCH MOLECULES

(71) Applicant: CITY OF HOPE, Duarte, CA (US)

(72) Inventors: John J. Rossi, Azusa, CA (US); Nan-Sook Lee, Pasadena, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 14/590,499

(22) Filed: Jan. 6, 2015

(65) Prior Publication Data
US 2015/0118682 A1 Apr. 30, 2015

Related U.S. Application Data

(60) Continuation of application No. 14/164,625, filed on Jan. 27, 2014, now Pat. No. 8,927,519, which is a continuation of application No. 13/324,104, filed on Dec. 13, 2011, now abandoned, which is a continuation of application No. 12/881,509, filed on Sep. 14, 2010, now Pat. No. 8,076,071, which is a division of application No. 10/365,643, filed on Feb. 13, 2003, now Pat. No. 7,820,632.

(60) Provisional application No. 60/356,127, filed on Feb. 14, 2002.

(51) Int. Cl.
| | |
|---|---|
| C12Q 1/68 | (2006.01) |
| C07H 21/02 | (2006.01) |
| C07H 21/04 | (2006.01) |
| C12N 15/11 | (2006.01) |
| C12N 15/113 | (2010.01) |
| C12N 5/00 | (2006.01) |

(52) U.S. Cl.
CPC ............ *C12Q 1/6876* (2013.01); *C12N 15/111* (2013.01); *C12N 15/113* (2013.01); *C12N 15/1132* (2013.01); *C12N 2310/111* (2013.01); *C12N 2310/14* (2013.01); *C12N 2310/53* (2013.01); *C12N 2330/30* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 5,624,803 A | 4/1997 | Noonberg et al. | |
| 6,506,559 B1 | 1/2003 | Fire et al. | |
| 6,573,099 B2 | 6/2003 | Graham | |
| 7,294,504 B1 | 11/2007 | Wang | |
| 7,422,896 B1 | 9/2008 | Wang | |

| | | | |
|---|---|---|---|
| 2002/0086356 A1 | 7/2002 | Tuschl et al. | |
| 2002/0114784 A1 | 8/2002 | Li et al. | |
| 2002/0173478 A1 | 11/2002 | Gewirtz | |
| 2003/0059943 A1 | 3/2003 | Certa et al. | |
| 2003/0084471 A1 | 5/2003 | Beach et al. | |
| 2003/0144232 A1 | 7/2003 | Agami et al. | |
| 2003/0198627 A1 | 10/2003 | Arts et al. | |
| 2004/0002077 A1 | 1/2004 | Taira et al. | |
| 2004/0259247 A1 | 12/2004 | Tuschl et al. | |
| 2005/0048647 A1 | 3/2005 | Taira et al. | |
| 2006/0009402 A1 | 1/2006 | Zamore et al. | |

FOREIGN PATENT DOCUMENTS

| | | |
|---|---|---|
| EP | 1 462 525 A1 | 9/2004 |
| JP | 2001-363385 A1 | 9/2005 |
| WO | 00/63364 A2 | 10/2000 |
| WO | WO 02/44321 A2 | 6/2002 |
| WO | WO 03/022052 A1 | 3/2003 |
| WO | 03/057840 A2 | 7/2003 |

OTHER PUBLICATIONS

Hammond, Scott M., et al., "An RNA-directed nuclease mediates post-transcriptional gene silencing in *Drosophila* cells," *Nature* 404:293-296, Mar. 16, 2000.
Lee, Nan Sock, et al., "Functional colocalization of ribozymes and target mRNAs in *Drosophila* oocytes," *The FASEB Journal* 15: 2390-2400, Nov. 2001.
Clemens, James C., et al., "Use of double-stranded RNA interference in *Drosophila* cell lines to dissect signal transduction pathways," *PNAS* 97(12):6499-6503, Jun. 6, 2000.
Lipardi, Concetta, et al., "RNAi as Random Degradative PCR: siRNA Primers Convert mRNA into dsRNAs that are Degraded to Generate New SiRNAs," *Cell* 107: 297-307, Nov. 2, 2001.
Sijen, Titia, et al., "On the Role of RNA Amplification in dsRNA-Triggered Gene Silencing," *Cell* 107: 465-476, Nov. 16, 2001.
Elbashir, Sayda M., et al., "RNA interference is mediated by 21- and 22-nucleotide RNAs," *Gene & Development* 15:188-200, 2001.
Wianny, Florence, et al, "Specific interference with gene function by double-stranded RNA in early mouse development," *Nature Cell Biology* 2:70-75, Feb. 2000.
Kennerdell, Jason R., et al., "Use of dsRNA-Mediated Genetic Interference to Demonstrate that frizzled and frizzled 2 Act in the Wingless Pathway," *Cell* 95:1017-1026, Dec. 23, 1998.
Fire, Andrew, et al, "Potent and specific genetic interference by double-stranded RNA in *Caenorhabditis elegans*," *Nature* 391:806-811, Feb. 19, 1998.
Fire, Andrew, et al, "RNA-triggered gene silencing," *TIG* 15(9):358-363, Sep. 1999.
Svoboda, Petr, et al, "Selective reduction of dormant maternal mRNAs in mouse oocytes by RNA interference," *Development* 127:4147-4156, 2000.
Elbashir, Sayda M., et al., "Duplexes of 21-nucleotide RNAs mediate RNA in cultured mammalian cells," *Nature* 411:494-498, May 24, 2001.
Bertrand, Edouard, et al, "The expression cassette determines the functional activity of ribozymes in mammalian cells by controlling their intracellular localization," *RNA* 3:75-88, 1997.
Good, PD, et al., "Expression of small, therapeutic RNAs in human cell nuclei," *Gene Therapy* 4:45-54, 1997.

(Continued)

*Primary Examiner* — Sean McGarry
(74) *Attorney, Agent, or Firm* — Rothwell, Figg, Ernst & Manbeck P.C.

(57) ABSTRACT

Methods for producing interfering RNA molecules in mammalian cells are provided. Therapeutic uses for the expressed molecules, including inhibiting expression of HIV, are also provided.

7 Claims, 8 Drawing Sheets

(56) References Cited

OTHER PUBLICATIONS

Scherr, Michaela, et al, "Rapid determination and quantitation of the accessibility to native RNAs by antisense oligideoxynucleotides in murine cell extracts," *Nucleic Acids Research* 26(22):5079-5085, 1998.

Barton, Gregory M., et al, "Retroviral delivery of small interfering RNA into primary cells," *PNAS* 99(23): 14943-14945, Nov. 12, 2002.

Brummelkamp, Thijn R., et al, "A System for Stable Expression of Short Interfering RNAs in Mammalian Cells," *Science* 296:550-553, Apr. 19, 2002.

Devroe, Eric, et al., "Retrovirus-delivered siRNA," *BMC Biotechnology* 2:1-5, Aug. 28, 2002.

Paul, Cynthia P., et al., "Effective expression of small interfering RNA in human cells," *Nature Biotechnology* 29:505-508, May 2002.

Yu, Jenn-Yah, et al., "RNA Interference by expression of short-interfering RNAs and hairpin RNAs in mammalian cells," *PNAS* 99(9):6047-6052, Apr. 30, 2002.

Leirdal, Marianne, et al., "Gene silencing in mammalian cells by preformed small RNA duplexes," *Biochemical and Biophysical Research Communications* 295:744-748, 2002.

Ui-Tei, Kumiko, et al., "Sensitive assay of RNA interference in *Drosophila* and Chinese hamster cultured cells using firefly luciferase gene as target," *FEBS Letters* 479:79-82, 2000.

Scherr, Michaela, et al., "Detection of Antisense and Ribozyme Accessible Sites on Native mRNAs: Application to NCOA3 mRNA," *Molecular Therapy* 4(5):454-460, Nov. 2001.

Lee, Nan Sook, et al., "mRNA localization signals can enhance the intracellular effectiveness of hammerhead ribozymes," *RNA* 5:1200-1209, 1999.

Sharp, Philip A., "RNA interference-2001," *Genes & Development* 15:485-490, 2001.

Caplen, Natasha J., et al., "Specific inhibition of gene expression by small double-stranded RNAs in invertebrate and vertebrate systems," *PNAS* 98(17):9742-9747, Aug. 14, 2001.

Tuschl et al., "Expanding small RNA interference," *Nature Biotechnology* 20:446-448, May 2002.

Paddison et al., "Short hairpin RNAs (shRNAs) induce sequence-specific silencing in mammalian cells," *Genes and Development* 16:948-958, Mar. 2002.

Shinagawa et al., "Generation of Ski-knockdown mice by expressing a long double-strand RNA from an RNA polymerase II promoter," *Genes and Development* 17:1340-1345, Apr. 2003.

Kawasaki et al., "Short hairpin type of dsRNAs that are controlled by tRNA$^{Val}$ promoter significantly induce RNAi-mediated gene silencing in the cytoplasm of human cells," *Nucleic Acids Research* 31(2):700-707, Jan. 2003.

Miyagishi et al., "U6 promoter-driven siRNAs with four uridine 3' overhangs efficiently suppress targeted gene expression in mammalian cells," *Nature Biotechnology* 19:497-500, May 2002.

Lee et al., "Expression of small interfering RNAs targeted against HIV-1 rev transcripts in human cells," *Nature Biotechnology* 19:500-505, May 2002.

Shi, Y., "Mammalian RNAi for the masses," *Trends in Genetics* 19(1):9-12, Jan. 2003.

Ding et al., Nucleic Acids Research, vol. 26(13): 1998.

Opposition Against EP-B1 1 483 281 (03 70 7861.5), Patentee: City of Hope, Opposition by: Dr. Roland Lammert, excerpt from EPO Register, date for registration to withdraw: Jan. 6, 2009, 3 pages.

Opposition Against EP-B1 1 483 281 (03 70 7861.5), Patentee: City of Hope, Opposition by: Dr. Roland Lammert, Certified Priority Document, U.S. Appl. No. 60/343,697; dated Feb. 12, 2003, 46 pp.

Sui, G., et al., "A DNA vector-based RNAi technology to suppress gene expression in mammalian cells," PNAS, Apr. 16, 2002, vol. 99, No. 8, pp. 5515-5520.

Good, P.D., et al., Expression of small, therapeutic RNAs in human cell nuclei, Gene Therapy, 1997, vol. 4, pp. 45-54.

Scherr, M., et al., "Gene Silencing Mediated by Small Interfering RNAs in Mammalian Cells", Current Medicinal Chemistry, 2003, vol. 10, pp. 245-256.

Japanese Office Action dated Nov. 6, 2008, JP Application No. 2003-567923, 3 pages.

Jayan, G.C., Research Article, "SV40-derived vectors provide effective transgene expression and inhibition of HIV-1 using constitutive, conditional, and pol III promoters," Gene Therapy 8:1033-1042, 2001, 10 pages.

Tavernarakis, N., "Heritable and inducible genetic interference by double-stranded RNA encoded by transgenes," Nature Genetics 24:180-183, 2000, 4 pages.

Notice of Opposition to a European Patent, Patent No. EP 1 483 281, Application No. EP 03 70 7861.5, Date of Mention of Grant, Sep. 3, 2008, "Methods for Producing Interfering RNA Molecules in Mammalian Cells and Therapeutic Uses for Such Molecules," Assignee: City of Hope, Opponent: Dr. Roland Lambert, 33 pages.

Opposition against EP-B1 1 483 281; Patentee: City of Hope; Opposition by Dr. Roland Lammert, except from EPO Register WO03057840 published Jul. 17, 2003, 3 pages.

Opposition against EP-81 1 483 281; Patentee: City of Hope; Opposition by Dr. Roland Lammert, English translation of JP-2001-363385 filed on Nov. 28, 2001, 47 pages.

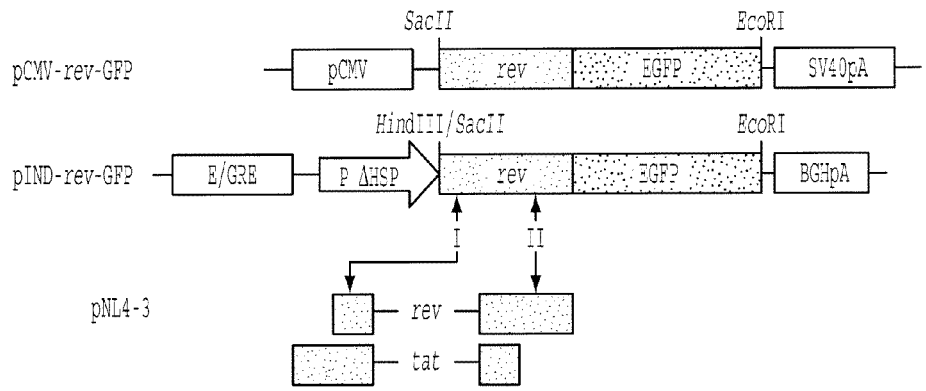
FIG. 1A
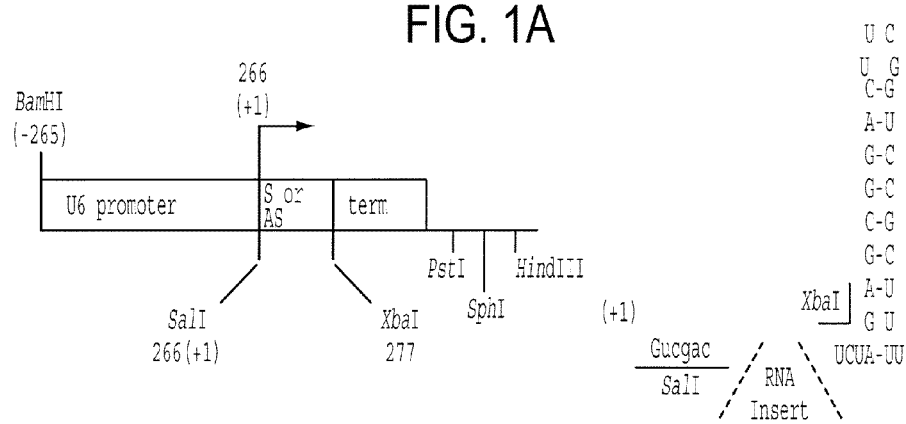
FIG. 1B
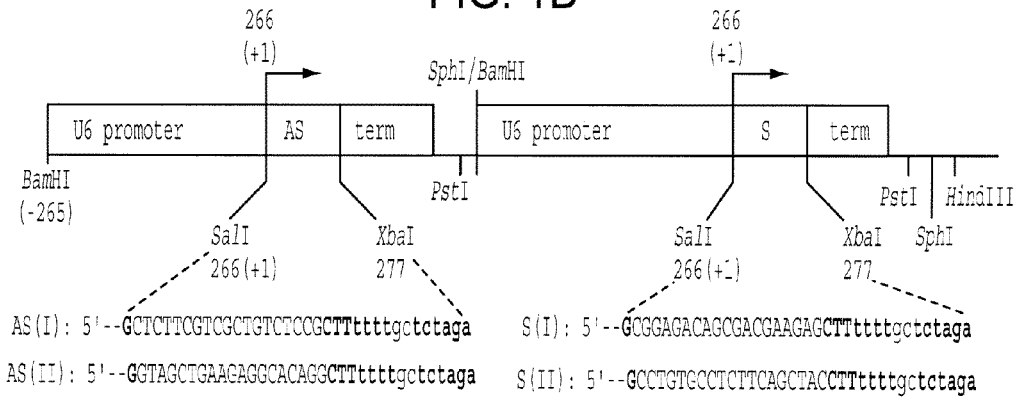
FIG. 1C
FIG. 1D

METHODS FOR PRODUCING INTERFERING RNA MOLECULES IN MAMMALIAN CELLS AND THERAPEUTIC USES FOR SUCH MOLECULES

CROSS-REFERENCE TO RELATED APPLICATIONS

The present application is a continuation of U.S. patent application Ser. No. 14/164,625 filed 27 Jan. 2014, which in turn is a continuation of U.S. patent application Ser. No. 13/324,104 filed 13 Dec. 2011, which in turn is a continuation of U.S. patent application Ser. No. 12/881,509 filed 14 Sep. 2010, now U.S. Pat. No. 8,076,071, which in turn is a division of U.S. patent application Ser. No. 10/365,643 filed 13 Feb. 2003, now U.S. Pat. No. 7,820,632, which in turn relates to and claims priority under 35 U.S.C. §119(e) to U.S. provisional patent application Ser. No. 60/356,127, filed 14 Feb. 2002. Each application is incorporated herein by reference

REFERENCE TO GOVERNMENT SUPPORT

This invention was made with government support under Grant No. A1 29329 awarded by the National Institutes of Health. The United States government has certain rights in the invention.

SEQUENCE SUBMISSION

The present application is being filed along with a Sequence Listing in electronic format. The Sequence Listing is entitled 1954577SequenceListing.txt, created on 5 Jan. 2015 and is 3 kb in size. The information in the electronic format of the Sequence Listing is part of the present application and is incorporated herein by reference in its entirety.

FIELD OF THE INVENTION

The present invention relates to RNA interference. More particularly, the present invention relates to methods for producing interfering RNA molecules in mammalian cells, and genetic and therapeutic uses for such expressed molecules.

BACKGROUND OF THE INVENTION

RNA interference is the process of sequence-specific, post-transcriptional gene silencing in animals and plants initiated by double stranded (ds) RNA that is homologous to the silenced gene (Hammond, S. M. et al., 2000; Fire, A., 1999; Sharp, P. A., 2001). In particular, synthetic and endogenous siRNAs are known to direct targeted mRNA degradation (Hammond, S. M. et al., 2000; Elbashir, S. M. et al., 2001; Caplen, N. J. et al., 2001; Clemens, J. C. et al., 2000; Lipardi, C. et al., 2001; Elbashir, S. M. et al., 2001; Ui-Tei, K. et al., 2000).

This powerful genetic technology has usually involved injection or transfection of ds RNA in model organisms. RNA interference also is a potent inhibitor of targeted gene expression in a variety of organisms (Wianny, F. et al., 2000; Kennerdell, J. R. et al., 1998; Fire, A. et al., 1998; Oelgeschlager, M. et al., 2000; Svoboda, P. et al., 2000). Recent studies by several groups (Lipardi, C. et al., 2001; Sijen, T. et al., 2001) suggest that ds small interfering RNAs (siRNAs) are part of a riboprotein complex that includes an RNAse III-related nuclease (Dicer) (Bernstein, E. et al., 2001), a helicase family (Dalmay, T. et al., 2001; Cogoni, C. et al., 1999), and possibly a kinase (Nykanen, A. et al., 2001) and an RdRP (Lipardi, C. et al., 2001; Smardon, A. et al., 2000). The mechanism proposed by Lipardi et al. (Lipardi, C. et al., 2001) is that one of the siRNA oligomers (antisense to the target RNA) primes an RdRP, generating longer dsRNAs, which are then cleaved by the RNAse III activity into additional siRNA duplexes, thereby amplifying the siRNAs from the target template.

dsRNA≥30 bp can trigger in mammalian cells interferon responses that are intrinsically sequence-nonspecific (Elbashir, S. M. et al., 2001). However, duplexes of 21-nucleotide (nt) siRNAs with short 3' overhangs can mediate RNA interference in a sequence-specific manner in cultured mammalian cells (Elbashir, S. M. et al., 2001). Two groups have demonstrated that 19 to 21 base duplexes with 3'UU or TT overhangs can effectively elicit an siRNA response in mammalian cells (Elbashir, S. M. et al., 2001; Caplen, N. J. et al., 2001). However, one limitation to the use of siRNA as a therapeutic reagent in vertebrate cells is that short, highly defined RNAs need to be delivered to target cells, which thus far has been accomplished only by using synthetic, duplexed RNAs delivered exogenously to cells (Elbashir, S. M. et al., 2001; Caplen, N. J. et al., 2001).

The present invention overcomes at least the above limitation.

SUMMARY OF THE INVENTION

In one aspect, the present invention provides methods for producing double stranded, interfering RNA molecules in mammalian cells, and preferably human cells, by introducing into the cells DNA sequences encoding the interfering RNA molecules.

In another aspect, the method comprises a) inserting DNA sequences encoding a sense strand and an antisense strand of an interfering RNA molecule into a vector comprising a suitable promoter, preferably a RNA pol III promoter, and b) introducing the vector into a mammalian cell so that the RNA molecule can be expressed.

In a preferred embodiment, the present invention includes first selecting a target sequence, which preferably is accessible to the pairing between the target sequence and interfering RNA required for the interfering RNA to function properly. Methods for identifying target sites may be carried out using synthetic DNA oligonucleotides in cell extracts and/or a site selection approach on native RNAs, as described herein. Once an optimal target site has been identified, the appropriate sequences for making the sense and antisense strands of the interfering RNA molecule can be synthesized.

Possible target sites include those found on the transcription products of cellular or infectious agent genes (viral, bacterial etc.).

In another preferred embodiment, the RNA molecule produced is a small interfering RNA (siRNA) molecule, while the DNA sequences encoding the sense and antisense strands of the siRNA are siDNA.

In another preferred embodiment, the RNA pol III promoter is a mammalian U6 promoter, and more preferably the human U6 RNA Pol III promoter.

In another aspect, the invention provides methods for inhibiting the expression of target genes, comprising introducing one or more vectors into a mammalian cell, wherein the one or more vectors comprise a suitable promoter and DNA sequences encoding a sense strand and an antisense strand of an interfering RNA, preferably siRNA, molecule. The interfering RNA molecule, which preferably is specific for the transcription product of the target gene, can be then expressed and initiate RNA interference of protein expression of the target gene in the mammalian cell, thereby inhibiting expression of the target gene.

In another aspect, the invention provides a method for testing the expression and function of siRNA molecules, comprising co-introducing into a mammalian cell i) one or more vectors comprising a suitable first promoter and DNA sequences encoding a sense strand and an antisense strand of an siRNA molecule, and ii) a vector comprising a target gene and a suitable second promoter. The siRNA molecule can be then expressed and initiate RNA interference of expression of the target gene, thereby potentially inhibiting expression of the target gene. Thus, the endogenous expression and function of the siRNA molecule can be assayed based on the presence, if any, of RNA interference and more particularly by any inhibition of expression of the target gene.

The present invention thus provides many possible therapeutic applications, based on the design of the siRNA molecules and their specificity for selected disease targets. For example, one application of the invention is the treatment of HIV, for which siRNA molecules may be designed to inhibit the expression of selected HIV targets, thus inhibiting HIV expression.

In a preferred embodiment, the invention provides a method for inhibiting expression of an HIV target gene, comprising introducing one or more vectors into a mammalian cell, preferably an HIV-infected human cell. The one or more vectors comprise a suitable promoter and DNA sequences encoding a sense strand and an antisense strand of an siRNA molecule, which preferably is specific for the transcription product of the HIV target gene. More preferably, the siRNA molecule is specific for a selected target site on the transcription product of the selected HIV target gene. The siRNA molecule can be then expressed and initiate RNA interference of expression of the target gene, thereby inhibiting expression of the target gene.

In a more preferred embodiment, the HIV is HIV-1. In another preferred embodiment, multiple siRNA constructs targeted to different sites in the HIV genome may be expressed, thereby initiating RNA interference of expression of several different HIV target genes and thus possibly circumventing genetic resistance of the virus.

BRIEF DESCRIPTION OF THE FIGURES

FIG. 1A shows a schematic diagram of a target rev-EGFP construct.

FIG. 1B (SEQ ID NO:9) and 1C (AS(I) (SEQ ID NO:1), S(I) (SEQ ID NO:2), AS(II) (SEQ ID NO:3), S(II) (SEQ ID NO:4)) show schematic diagrams of a U6 promoter construct and a U6 promoter driven siRNA construct.

FIG. 1D shows siRNAs (S(I) (SEQ ID NO:5), AS(I) (SEQ ID NO:6), S(II) (SEQ ID NO:7), AS(II) (SEQ ID NO:8) in accordance with an embodiment of the invention.

DETAILED DESCRIPTION OF THE INVENTION

Figure 2:
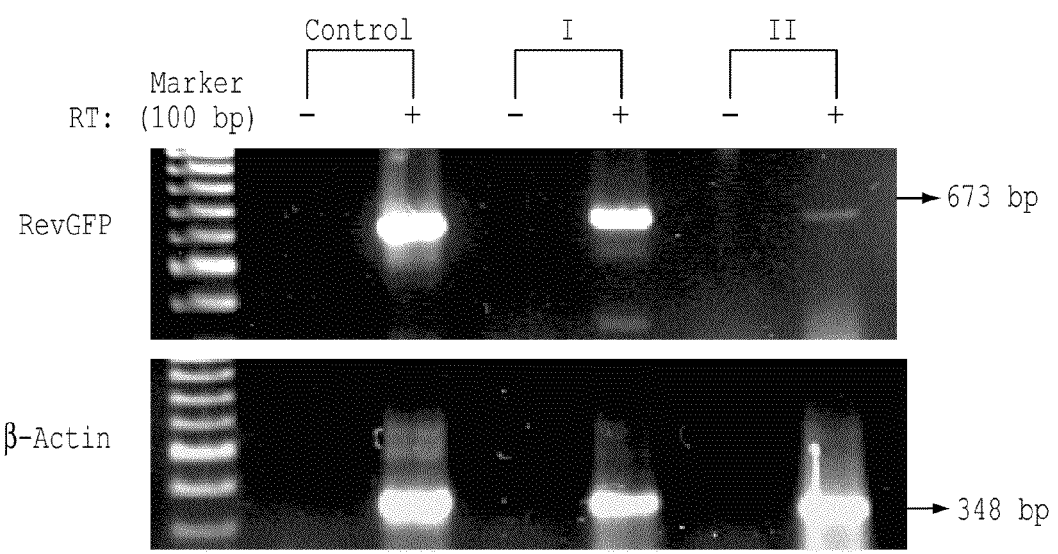
FIG. 2 shows gel photographs from accessibility assays for sites I and II in cell extracts prepared from rev-EGFP expressing cells.
Figure 3A:
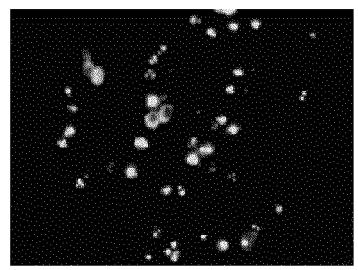
FIGS. 3A to 3J show photographs obtained from fluorescent microscope imaging of the effect of siRNA on EGFP expression.
Figure 3F:
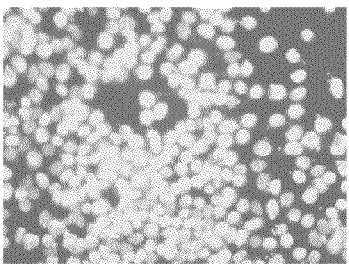
Figure 3B:
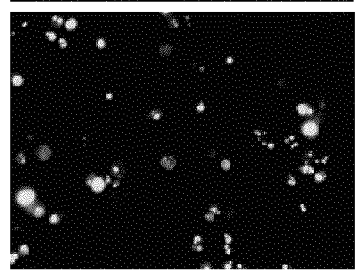
Figure 3G:
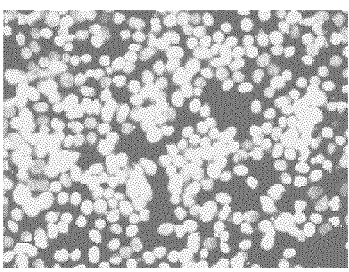
Figure 3C:
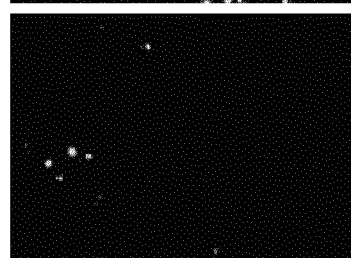
Figure 3H:
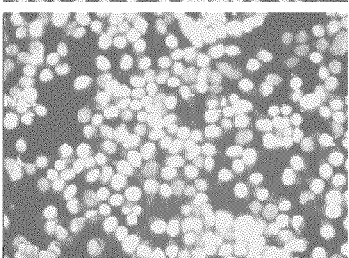
Figure 3D:
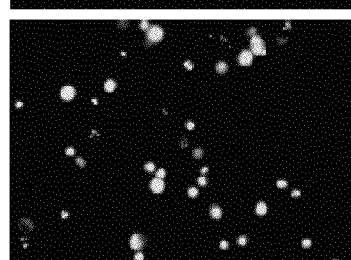
Figure 3I:
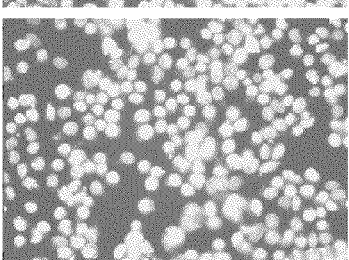
Figure 3E:
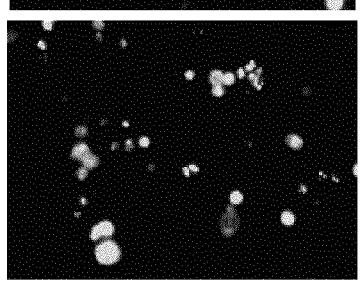
Figure 3J:
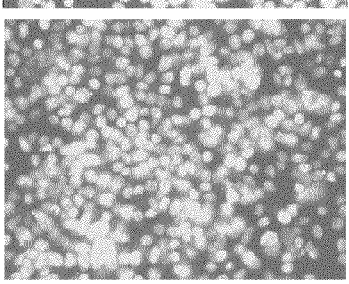

Interfering RNA molecules, and more preferably siRNA molecules, produced and/or used in accordance with the invention include those types known in the art. The interfering RNA, and preferably siRNA, molecules are double-stranded (ds) RNAs that preferably contain about 19 to 23 base pairs. The molecules also may contain 3' overhangs, preferably 3'UU or 3'TT overhangs.

The term "introducing" encompasses a variety of methods of introducing DNA into a cell, either in vitro or in vivo, such methods including transformation, transduction, transfection, and infection. Vectors are useful and preferred agents for introducing DNA encoding the interfering RNA molecules into cells. Possible vectors include plasmid vectors and viral vectors. Viral vectors include retroviral vectors, lentiviral vectors, or other vectors such as adenoviral vectors or adeno-associated vectors.

In one embodiment, the DNA sequences are included in separate vectors, while in another embodiment, the DNA sequences are included in the same vector. If the DNA sequences are included in the same vector, the DNA sequences may also be inserted into the same transcriptional cassette.

Alternative delivery systems for introducing DNA into cells may also be used in the present invention, including, for example, liposomes, as well as other delivery systems known in the art.

Suitable promoters include those promoters that promote expression of the interfering RNA molecules once operatively associated or linked with sequences encoding the RNA molecules. Such promoters include cellular promoters and viral promoters, as known in the art. In one embodiment, the promoter is a RNA pol III promoter, which preferably is located immediately upstream of the DNA sequences encoding the interfering RNA molecule. Various viral promoters may be used, including, but not limited to, the viral LTR, as well as adenovirus, SV40, and CMV promoters, as known in the art.

In a preferred embodiment, the invention uses a mammalian U6 RNA Pol III promoter, and more preferably the human U6snRNA Pol III promoter, which has been used previously for expression of short, defined ribozyme transcripts in human cells (Bertrand, E. et al., 1997; Good, P. D. et al., 1997). The U6 Pol III promoter and its simple termination sequence (four to six uridines) were found to express siRNAs in cells. Appropriately selected interfering RNA or siRNA encoding sequences can be inserted into a transcriptional cassette, providing an optimal system for testing endogenous expression and function of the RNA molecules.

In a preferred embodiment, the mammalian cells are human cells. However, it is also understood that the invention may be carried out in other target cells, such as other types of vertebrate cells or eukaryotic cells.

In accordance with the invention, effective expression of siRNA duplexes targeted against the HIV-1 rev sequence was demonstrated. Using a rev-EGFP (enhanced green fluorescent protein) fusion construct in transient co-transfection assays, ca 90% inhibition of expression was observed. The same siRNA expression constructs have been tested against HIV in co-transfection assays resulting in a four-log reduction in HIV p24 antigen levels.

The above results were achieved using a human U6 snRNA Pol III promoter to express the appropriate 21 base oligomer RNAs in human cells. The promoter design is such that the first base of the transcript is the first base of the siRNA, and the transcript terminates within a run of 6 U's encoded in the gene. The U6+1 promoter initiates transcription with a triphosphate, and the transcript is not capped unless the first 27 bases of the U6 RNA are included in the transcript (Bertrand, E. et al., 1997; Good, P. D. et al., 1997). Thus, it was believed that siRNAs could be made whose structure would closely mimic certain predefined requirements (Elbashir, S. M. et al., 2001; Caplen, N. J. et al., 2001).

As stated above, expression cassettes are designed such that sequences encoding sense and antisense strands of the siRNA can be in either the same or separate vectors. Although the vector containing both sense and antisense strands was predicted to be superior to co-transfecting the two separately, this was not the case. It is likely that the co-transfection juxtaposes the two sequences so that transcripts have ample opportunity to form dsRNAs. An interesting feature of the expression system is that in cells expressing both sense and antisense RNA oligomers, an unexpected aberrantly sized product accumulates in large amounts (FIGS. 5A-D). Experiments with RNAse pretreatment of the RNAs prior to electrophoresis and blotting suggest that this larger transcript is double stranded. The ds RNA may be in the form of a simple duplex, or could be covalently joined. Covalently linked siRNAs have been shown to be effective when expressed in cells, a result somewhat contradictory to the results when using ex vivo delivered siRNAs (Elbashir, S. M. et al., 2001; Caplen, N. J. et al., 2001).

In order to ascertain whether or not there are differences in target site accessibilities for siRNA pairing as observed for antisense oligos and ribozymes (Scherr, M. et al., 1998; Scherr, M. et al., 2001; co-pending U.S. application Ser. No. 09/536,393, filed Mar. 28, 2000), two target sites for the siRNAs were tested. One site was chosen by an oligonucleotide library scanning mechanism designed to identify sites accessible to antisense pairing on native RNAs in cell extracts (Scherr, M. et al., 2001), whereas the other site was chosen at random in a segment of rev that overlaps with the HIV-1 tat sequence. Marked differences in accessibility to oligo pairing to these two sites translated to marked differences in siRNA inhibitory activities in the rev-EGFP fusion. Despite the differences in potency against the rev-EGFP target, both siRNAs were potent inhibitors in HIV-1 co-transfection assays. The invention thus demonstrates functional intracellular expression of siRNAs in mammalian cells, particularly human cells.

An interesting result was the relationship between antisense DNA oligomer site-accessibility and the efficacy of the siRNAs targeted against the rev-EGFP transcript. More specifically, there was observed a relative lack of inhibition of the rev-EGFP target mediated by site I siRNAs. This result was not the result of poor expression of these oligomers, since they appear to be expressed in equivalent amounts to site II siRNAs (FIGS. 5A-D). These differing results could be due to the position of the siRNA target site relative to the end of the target transcript, which has been demonstrated to limit amplification of the siRNAs in *Drosophila* (Elbashir, S. M. et al., 2001). However, this does not seem to be the case since site I is positioned 301 nts downstream of the pIND-rev-EGFP transcriptional start site, which is well beyond the minimal distance required to amplify the siRNAs. These results could be due to different targets used in different experiments. The relative accessibility of the site I in the context of the rev-EGFP fusion mRNA may be limiting as shown by oligo-RNAseH experiments (FIG. 2). In the HIV-1 transcripts, site I is present in both the tat and rev transcripts, as well as in the singly spliced and unspliced transcripts. Given the complexity of different transcripts harboring site I, it is not possible to state which of these is sensitive to the site I siRNAs.

Target mRNA for Testing siRNA.

A prerequisite for development of siRNA approaches to silence viral gene expression is to have an appropriate human cell assay system. In order to assay the siRNAs, rev was fused to EGFP (enhanced green fluorescent protein) to provide a reporter system for monitoring siRNA function (FIG. 1A). Temporal control of target mRNA expression was obtained by inserting the rev-EGFP fusion gene in the Ecdysone-inducible pIND vector system (Invitrogen) (FIG. 1A). It will be readily apparent to persons skilled in the art that alternative vector systems and promoters may be used for expressing selected target genes or target fusion genes during co-transfection assays.

In order to use the inducible system, a 293/EcR cell line was used, which was engineered to respond to the insect hormone analogue Ponasterone A. When the pIND-rev-EGFP vector was transfected into these cells followed by addition of the inducer, EGFP fluorescence was observed as early as 3 hr after addition of ponasterone A and continued for more than 100 hr. In the absence of ponasterone A, EGFP fluorescence was not observed.

In FIG. 1A, the relative locations of the two siRNA target sites in the rev-EGFP target are indicated, as are the locations of these two target sites in HIV transcripts from pNL4-3.

Target Site Accessibility in the Rev-EGFP Fusion Transcript.

It was previously demonstrated that synthetic DNA oligonucleotides in cell or ovary extracts can be used to identify sites accessible to base pairing by both antisense DNA and ribozymes (Scherr, M. et al., 1998; Scherr, M. et al., 2001; Lee, N. S. et al., 2001). Semi-random 19-mer DNA oligomer libraries (Scherr, M. et al., 2001) were used in cell extracts prepared from cells expressing the rev-EGFP mRNA transcripts. Using this approach to screen the entire rev sequence, only a single TdPCR product was identified (data not shown), which centered within the sequence 5'GCCTGTGCCTCT-TCAGCTACC 3' (SEQ ID NO:10), located 213 nts downstream from the AUG codon of rev and 494 nts downstream of the site of pIND transcription initiation. Since this sequence harbors a CUC hammerhead ribozyme cleavage motif, a hammerhead ribozyme was also synthesized that cleaves after the CUC site. This enabled a comparison between the inhibitory activity of the siRNA with a ribozyme expressed from the same promoter system. To determine whether or not there are differences in the siRNA mediated targeting of a given message, a second 21 nt site with a 5' G and 3' C was selected, which has a total GC content similar to site I. The requirements for a 5' G and 3' C are based on the first nucleotide of the pTZU6+1 transcript, which initiates with a G (FIGS. 1C & D). The second target sequence, 5'GCGGAGA-CAGCGACGAAGAGC3' (SEQ ID NO:11), is also located in an exon common to tat and rev, 20 nts downstream of the rev translational initiation codon, and 301 nts downstream of the pIND transcriptional initiation signal.

In FIG. 1B, the schematic presentation of the upstream promoter and transcript portion of the U6 expression cassette is shown with the sequences and depicted structure of the expected primary transcript. In FIG. 1C, the sequences of the 21 base sense and antisense inserts with a string of 6T's and XbaI are shown. The first G came from the mung bean-treated SalI of pTZU6+1 vector. The 6T's may be processed to the 2T's (capital letters) by the Pol III RNA polymerase. In FIG. 1D, the putative siRNAs derived from co-expression of the sense and antisense 21 mers (S/AS(I) or (I)), with 3' UU overhangs are depicted.

To determine whether the two target sequences were equally accessible to antisense pairing, two 21-mer DNA oligonucleotides complementary to each of the two siRNA target sites were synthesized and used as probes for accessibility to base pairing with the rev-EGFP fusion transcripts in cell extracts. It was demonstrated (FIG. 2) that site II is highly accessible to base pairing with its cognate oligo (89% reduction in RT-PCR product relative to the no oligo control). This was in contrast to the results obtained with the site I oligo, which reduced the rev-EGFP transcript by 27% relative to the control. Since these two sites have marked differences in their accessibilities to antisense pairing (FIG. 2), they provided a good test for the role that target accessibility plays in siRNA-mediated targeting.

In FIG. 2, the ethidium bromide-stained bands represent RT-PCR products from rev-EGFP (top, 673 nt) or beta Actin (bottom, 348 nt) mRNAs. The lanes from left to right are: control, no added oligo, minus (−) or plus (+) RT; oligonucleotide probing for site I (−) or (+) RT; oligonucleotide probing of site II (−) or (+) RT. The reduction in target mRNA is elicited by endogenous RNAse H activity as described previously (Scherr, M. et al., 1998).

Genes encoding siRNAs targeted to site I or II were inserted behind the Pol III U6 SnRNA promoter of pTZU6+1 (FIGS. 1B & C). The transcriptional cassettes were constructed such that they are either in the same or different vectors. The constructs in separate vectors provided a set of sense and antisense controls.

Reduction of Target Gene Expression.

Figure 4:
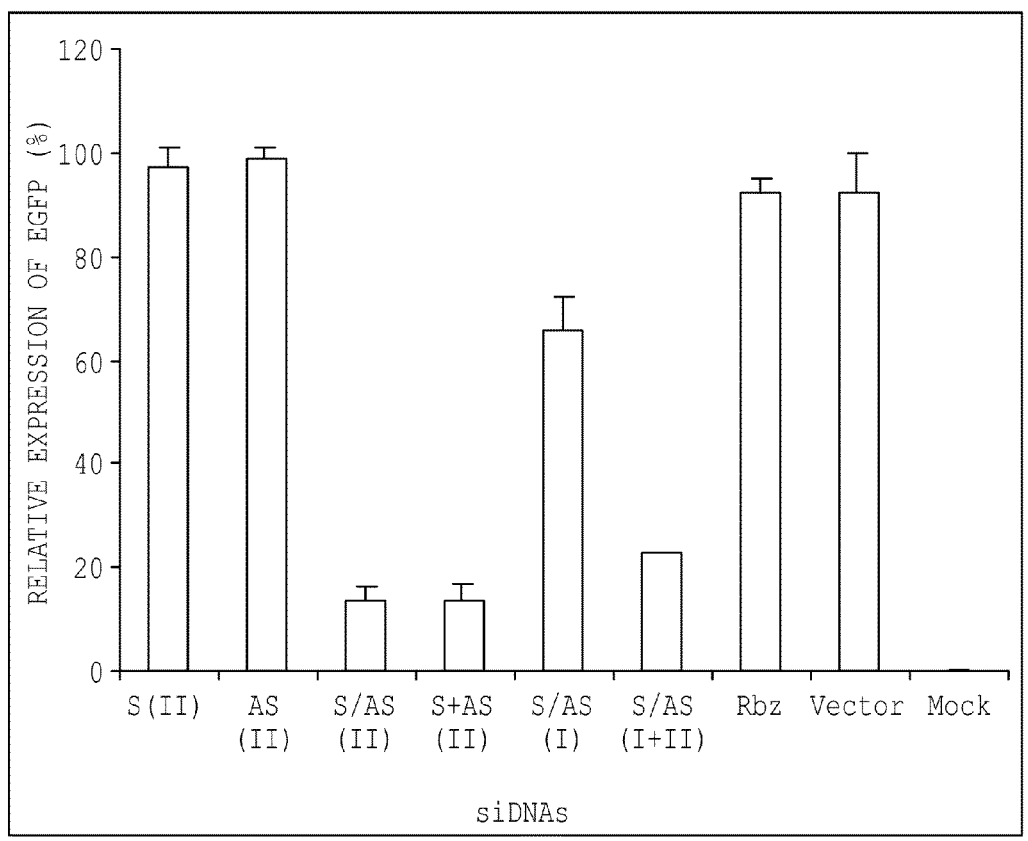
FIG. 4 is bar graph showing the extent of inhibition of EGFP expression by siRNAs in accordance with an embodiment of the invention.

The siRNA sequences, along with sense, antisense, or ribozyme controls were cotransfected with the target rev-EGFP expressing plasmid into 293/EcR cells. Sixteen to twenty hours later, the inducer Ponasterone A was added to the cell cultures resulting in induction of the rev-EGFP fusion product. The cells were incubated an additional 48 hours prior to fluorescent microscopic analyses and fluorescence activated cell sorting (FACS). Combined sense and antisense RNA oligomers targeted to site II in the rev sequence reduced the EGFP signal by ca 90% relative to the controls, whereas the combined sense and antisense RNA oligomers targeted against site I gave only a modest reduction in fluorescence (FIGS. 3 & 4). The inhibition mediated by the site II siRNAs was similar regardless of whether both sense and antisense RNA oligomers were expressed from the same plasmid or different plasmid backbones (see FIGS. 1B & C). The control constructs, which included sense alone, antisense alone or a ribozyme targeted to site II, each expressed from the U6 promoter, gave no significant reduction of EGFP expression relative to the vector backbone control (FIGS. 3 & 4).

In FIG. 3, 293/EcR cells were co-transfected with pIND-rev-EGFP and various siRNA constructs as indicated. Cells were examined microscopically for EGFP expression following Ponasterone A addition as described herein. Panel E shows fluorescent cells after transfection with control which is an irrelevant sense/antisense construct to the rev. Other types of controls (S(II), AS(II), vector) were similar (A, B, D). Panel C shows ~90% reduction in fluorescent cells when 293/EcR cells were transfected with S/AS(II). Panels F-J are DAPI-stained images showing that the same number of cells are present in each field. Specific silencing of target genes was confirmed in at least three independent experiments.

In FIG. 4, 293/EcR cells were co-transfected with pIND-rev-EGFP and siRNA constructs as described herein. Cells were analyzed for EGFP expression by FACS and the level of fluorescence relative to cells transfected with pIND-rev-EGFP alone was quantitated. Data are the average±SD of 3 separate experiments. Only the siRNA construct containing both sense and antisense sequences directed at accessible site II (S/AS(II) or S+AS(II)) showed approximately 90% reduction relative to the controls or vector only. The various combinations of U6 driven siRNA constructs co-transfected with pIND-rev-EGFP are indicated. S/AS indicates the vector with both sense and antisense siRNA sequence while S+AS indicates the siRNA sequences in separate vectors. Rbz indicates the hammerhead ribozyme against site II. Specific silencing of target genes was confirmed in at least three independent experiments.

Expression of siRNAs and Targets in 293 Cells.

Northern gel analyses were carried out to examine the expression patterns and sizes of the siRNAs transcribed from the U6 RNA Pol III promoter system in 293 cells. These Northern gel analyses demonstrated strong expression of sense and antisense RNAs as monitored by hybridization to the appropriate probes (FIG. 5).

In FIG. 5, RNA samples were prepared from 293/EcR cells transiently co-transfected with pIND-rev-GFP and various siRNA constructs as indicated and subjected to Ponasterone A induction as described above. The total RNA was resolved on a 10% acrylamide/8M urea gel for siRNAs, a 1% agarose/formamide gel for the target, or a 10% acrylamide/7M urea gel for RNAse A/T1 treatment. In FIGS. 5A to 5D, hybridization was performed using $^{32}P$ labeled DNA probes for sense or antisense transcripts for site I and II siRNAs. The hybridizing products were ~23- and ~46-nts in length. FIG. 5E shows the results of hybridization of the site II directed ribozyme (II) transcripts. RNAs prepared from cells expressing the ribozyme for site II detected a transcript of the size expected for the ribozyme transcript (~75 nt). Since the probe used to detect the ribozyme is also complementary to the antisense siRNA for site II, it also hybridized to the antisense RNAs targeted to site II.

The control RNAs (sense alone, antisense alone or ribozyme) were all detected at the expected sizes (FIGS. 5A-E). RNAs prepared from cells simultaneously expressing sense and antisense constructs generated hybridized products of the sizes expected for the individual short RNAs (~23 nts). In addition to the monomer sized RNAs, a strong hybridization product approximately twice the size of the short RNA oligomers (~46 nts) was clearly visible (FIGS. 5A-E). This product was only detected in RNAs prepared from cells expressing both sense and antisense, and hybridized with both sense and antisense probes (FIGS. 5A-E). Since the gel system used to resolve the transcripts was a denaturing gel, it seemed unlikely that the aberrantly sized product could be dsRNA. Nevertheless, to test this possibility, the RNA samples were treated with a mixture of RNAse A and T1 prior to denaturing gel electrophoresis and blotting. Both of these RNAses preferentially cleave single stranded RNAs. Thus, if the aberrant product is double stranded, it should be fully resistant to nuclease destruction. Two types of analyses were performed. The first involved simply treating the RNA samples with the RNAse mixture, whereas the second involved heating the samples to 95° C. prior to RNAse treatment (FIG. 5G).

Figure 5A:
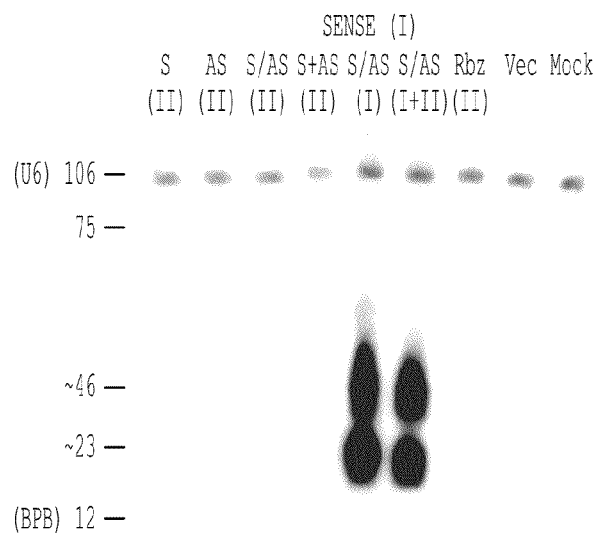
FIGS. 5A to 5G show autoradiographs of Northern gel analyses.
Figure 5B:
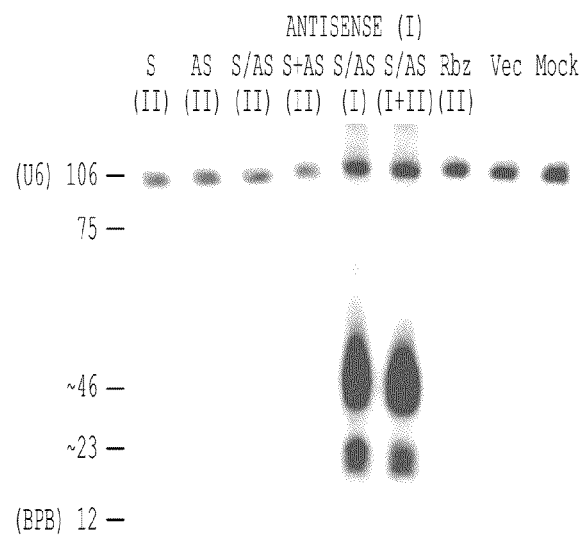
Figure 5C:
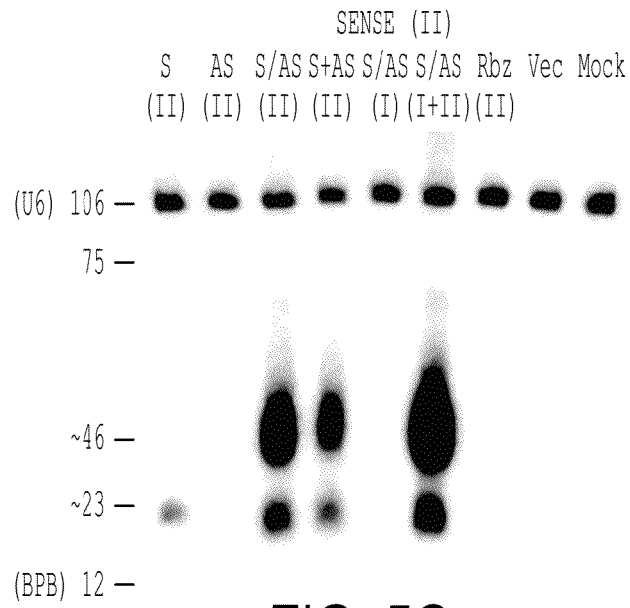
Figure 5D:
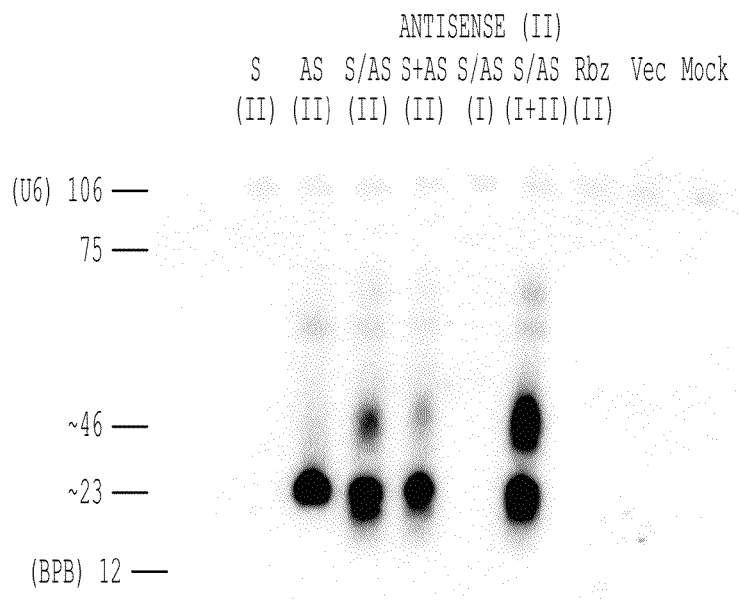
Figure 5E:
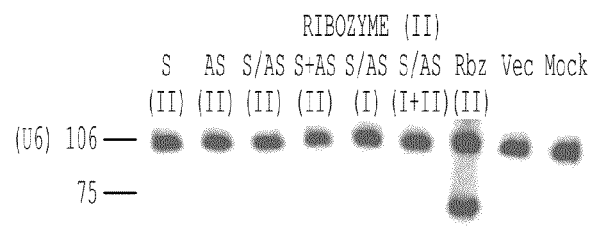
Figure 5F:
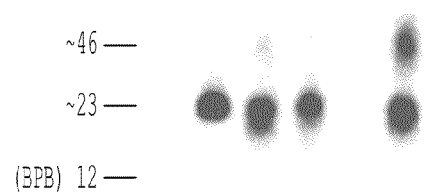
Figure 5G:
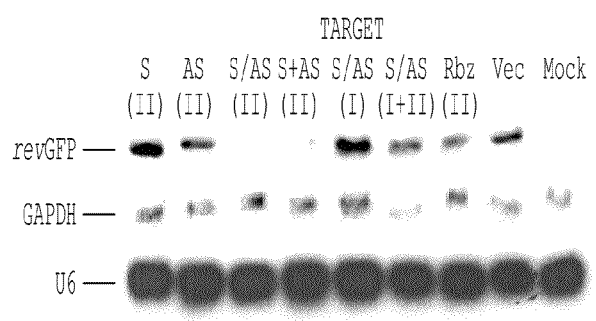

In FIG. 5G, the RNAs from a combined transfection using S/AS(I+II) were treated with a mixture of RNAse A and T1. Samples were either heated (+) or not heated (−) at 90° C. prior to RNAse treatment. The hybridizing product in the lane treated with RNAses, but without heat may be ~21 nts in length. This product was observed with probes for either sense or antisense siRNAs targeted to site II.

Fully duplexed RNAs should be resistant to cleavage, whereas heat treatment followed by quick cooling of the RNAs would separate the strands and make them susceptible to RNAse cleavage. The results obtained (FIG. 5G) were consistent with the aberrantly sized product being double stranded. The non-heated sample treated with the RNAse mix generated a product migrating faster than the other RNAs. The faster migrating RNA species hybridized to both the antisense and sense probes. In contrast, the sample that was heated prior to RNAse treatment gave no detectable hybridizing bands. The faster migration of this product could be due to RNAse trimming of non-base paired ends of the duplex. These products could also derive from RNAse cleavage of single stranded loops, which would unlink the two RNAs, allowing for faster gel mobility. Importantly, the large, aberrantly sized transcripts are only generated in cells expressing both sense and antisense transcripts, and therefore must be dependent upon formation of ds RNAs (Bernstein, E. et al., 2001; Clemens, J. C. et al., 2000). In addition to the aberrantly sized product, another band migrating between the aberrantly sized product and the 106 nt U6 snRNA was detected only with a probe that is complementary to the antisense siRNA for site II. This product was ~65 nts in length and could be a product of the first dicer cleavage reaction on an RNA dependent RNA polymerase (RdRP) extended product of the siRNA antisense (Lipardi, C. et al., 2001; Sijen, T. et al., 2001). Finally, U6+1 expression of the ribozyme targeted to site II (FIG. 5E) did not result in inhibition of rev-EGFP expression (FIG. 4).

To determine whether siRNA complexes directed degradation of the rev-EGFP mRNA, Northern hybridization analyses were carried out to probe for the rev-EGFP transcripts (FIG. 5F). FIG. 5F shows the results of hybridization of the rev-EGFP fusion transcripts. Human GAPDH mRNA and U6snRNA were probed as internal controls for each experiment. These data demonstrated selective destruction of the fusion transcript only in cells expressing the combination of site II sense and antisense siRNAs. The site I siRNAs, although abundantly expressed (FIGS. 5A and 5B) resulted in marginal inhibition of rev-EGFP expression (FIG. 4), with little degradation of the transcript (FIG. 5F). The combination of sites I and II siRNAs resulted in less inhibition than the site II siRNAs alone. This is believed to result from a dosage effect in that the concentration of each of the plasmids encoding these siRNAs was one half that used for the single site cotransfections. Most interestingly, the site I siRNAs were potent inhibitors of HIV replication.

Inhibition of HIV by Expressed siRNAs.

Figure 6:
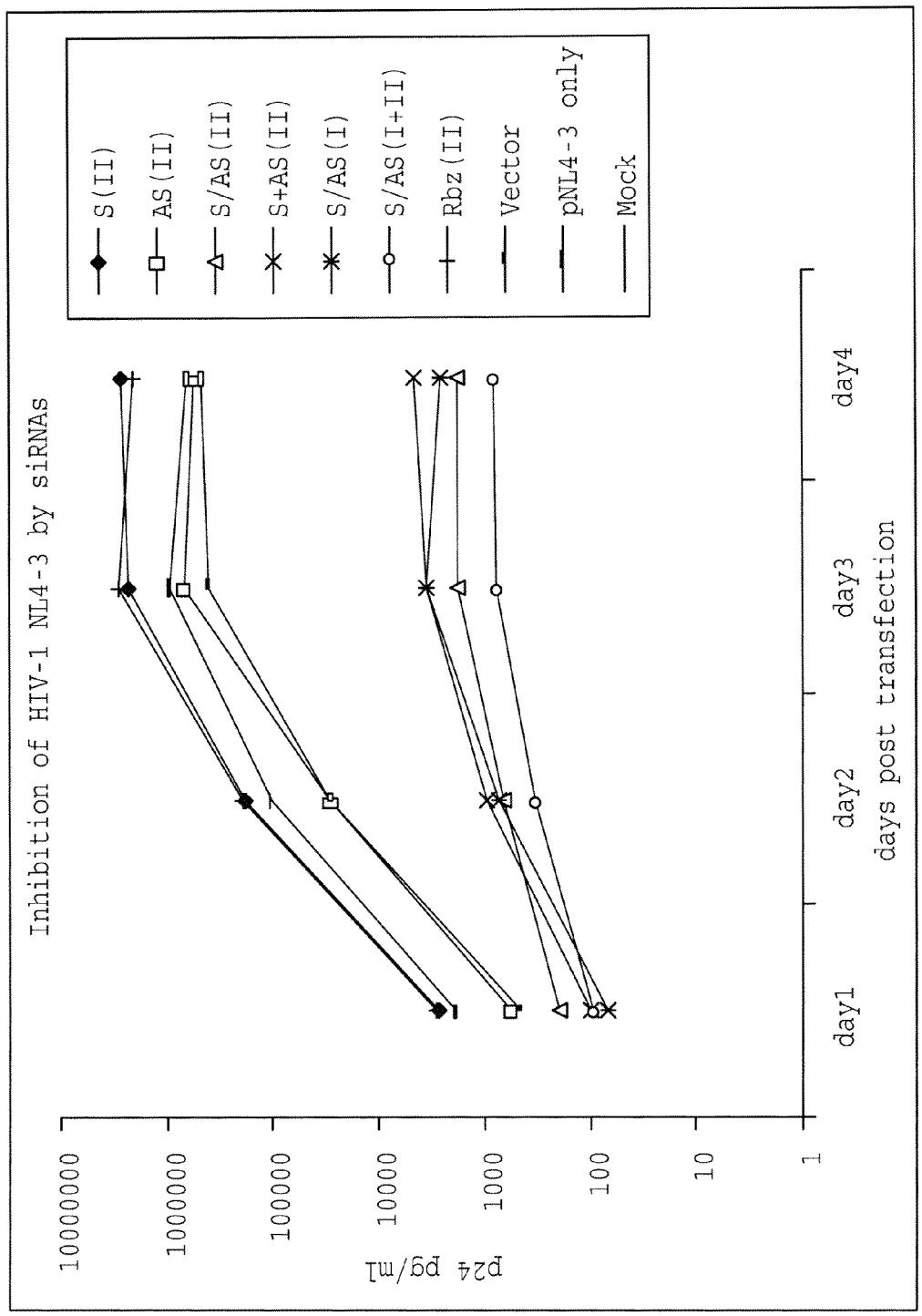
FIG. 6 is a graph showing inhibition of HIV-1 NL4-3 by siRNAs in accordance with an embodiment of the invention.

In another embodiment of the invention, an siRNA expression system was constructed for inhibiting HIV-1 infection. In order to test the potential inhibitory activity of the various constructs described above, each of the siRNA vectors (site I and II) as well as the control constructs were co-transfected with HIV-1 pNL4-3 proviral DNA into 293 cells. At the intervals indicated in FIG. 6, supernatant samples were withdrawn from the cell cultures and HIV-1 p24 viral antigen levels were measured. In FIG. 6, pNL4-3 proviral DNA was cotransfected with the various U6+1 driven siRNA constructs at 1:5 ratio of proviral DNA to U6 construct DNAs. Twenty-four hours post transfection, and at the indicated times, supernatant aliquots were withdrawn for HIV-1 p24 antigen assays. The various siRNA constructs used are indicated in FIG. 6.

The site II siRNAs were found to strongly inhibit HIV-1 replication in this assay. Somewhat unexpectedly, the site I siRNAs also potently inhibited HIV-1 replication (as measured by p24 antigen production). The combination of both site I and II siRNA constructs was the most potent, providing ca four logs of inhibition relative to the control constructs. Such potent inhibition of HIV-1 has not been previously observed with other RNA-based anti-HIV-1 agents using a co-transfection assay. Possible explanations for the differences in inhibitory activity by the site I siRNAs against the rev-EGFP fusion versus HIV-1 itself are addressed herein. The observation that two different HIV targets are both substrates for siRNA is highly encouraging for strategies requiring multiple targeting to circumvent genetic resistance of the virus.

The present invention is further illustrated by the following examples which are not intended to be limiting.

Example 1

Accessibility Assay

To evaluate the accessibility of target sequences for antisense base pairing, endogenous RNase H activity present in the cell extracts prepared from the stable 293 cells containing the rev-GFP was utilized. Two DNA oligonucleotides complementary to each of the two target sites were synthesized and used as probes for accessibility in cell extracts according to the protocol of Scherr, M. et al., 1998, as described herein, with some minor modifications.

Stable 293 cells containing CMV-revGFP gene were grown to 50 to 90% confluency in 100 mm dishes. Cells were harvested using a cell scraper and rinsed two times in phosphate buffered saline (PBS) twice. The cells were resuspended in the same volume of hypotonic swelling buffer (7 mM Tris-HCl, pH 7.5, 7 mM KCl, 1 mM $MgCl_2$, 1 mM β-mercaptoethanol) and ⅒th of the final volume of neutralizing buffer (21 mM Tris-HCl, pH 7.5, 116 mM KCl, 3.6 mM $MgCl_2$, 6 mM β-mercaptoethanol) on ice. The resuspended solutions were sonicated 15 seconds three times in an ice water bath. The homogenate was centrifuged at 20,000×g for 10 minutes at 4° C. The supernatants were used immediately, or stored as aliquots in the same volume of glycerol storage buffer (15 mM Tris-HCl, pH7.5, 60 mM KCl, 2.5 mM $MgCl_2$, 45% glycerol, 5 mM β-mercaptoethanol) at −80° C. These frozen aliquots were always used within 3 months post freezing.

The cell extracts were incubated with 4 μM of the respective 21 bp antisense oligodeoxyribonucleotides (site I or II) for 15 minutes at 37° C. in a total volume of 30 μl cleavage buffer (100 mM Tris-HCl, pH7.5, 100 mM $MgCl_2$, and 10 mM DDT). After phenol extraction and ethanol precipitation, the precipitates were digested with 20 U of DNase I for 45 minutes at 37° C., followed by phenol extraction and ethanol precipitation. The precipitates were resuspended in DEPC water and monitored for $OD_{260}$ absorption.

The reverse transcriptase (RT) reaction was carried out using 300 ng to 1 μg total RNA prepared from the above 30 μl extract sample with 5 U of Moloney murine leukemia virus reverse transcriptase (Mo-MLV Rtase, Life Technologies, Inc. NY) according to the manufacturer's instructions.

First-strand priming was performed with 20 pmol of 3' primer of an oligo complementary to the rev sequence or 50 ng of random hexamer primers. β-actin was used as an internal control. PCR reactions for each set of primers were performed separately in a total volume of 50 μl containing 10 mM Tris-HCl, pH 8.3, 50 mM KCl, 1.5 mM $MgCl_2$, 0.1 mM of each dNTP, 0.4 μM of each primer, 1.5 U of taq DNA polymerase and 2 μl of RT reaction sample. The PCR was carried out at 94° C. for 30 seconds, 68° C. for 30 seconds, and at 72° C. for 30 seconds for a total of 24 to 36 cycles after cycle studying of control.

Reaction samples were separated on a 1.2% agarose gel and visualized by ethidium bromide staining, then quantified using AlphaImager™ quantitation software (Alpha Innotech Corp.).

Example 2

Constructs

A SacII (filled in)-EcoRI fragment containing the rev-GFP fusion gene of CMV-rev-GFP was inserted into HindIII (filled in)-EcoRI sites of the pIND vector (Invitrogen), yielding the pIND-rev-GFP construct of (FIG. 1A).

To construct the siRNA expression vectors, two cassettes were prepared using the pTZ U6+1 vector (FIG. 1B). (Bertrand, E. et al., 1997; Good, P. D. et al., 1997). One cassette harbors the 21-nt sense sequences and the other a 21 nt antisense sequence. These sequences were designed to target either site I or site II (FIG. 1A). A string of 6T's was inserted at the 3' terminus of each of the 21 mers followed by a XbaI restriction site. The 20-nt sense or antisense sequences (excluding the first G) with a string of 6T's and the XbaI restriction site were prepared from synthetic oligonucleotides (Lee, N. S. et al., 2001; Lee, N. S. et al., 1999). The first G of the inserts was provide by the Sal I site of the vector which was rendered blunt-ended by mung bean nuclease. The inserts were digested by BsrBI for sense and AluI for antisense (site I), StuI for sense and SnaBI for antisense (site II) for blunt end cloning immediately downstream of the U6 promoter sequence. The 3' ends of the inserts were digested with Xba I for insertion in the Sal I (blunted)-Xba I digested pTZU6+1 vector to create the desired transcription units (FIG. 1C).

To create plasmids in which both sense and antisense sequences were in the same vector, the pTZU6+1 sense sequence harboring vectors were digested with BamHI (which was filled in using T4 DNA polymerase) and HindIII. The digested fragments containing the sense sequences were subcloned into the SphI (filled in by T4 DNA polymerase)-HindIII sites of the antisense AS(I) or AS(II) constructs, generating both sense and antisense transcription units (S/AS (I) or S/AS(II)) (FIG. 1C). The DNA sequences for each of the above constructs were confirmed prior to use.

Example 3

Cell Culture

293/EcR cells were grown at 37° C. in EMEM supplemented with 10% FBS, 2 mM L-glutamine and 0.4 mg/ml of Zeocine. Twenty-four hour before transfection, cells were replated to 24- or 6-well plates at 50-70% confluency with fresh medium without Zeocine. Co-transfection of target plasmids (pIND-rev-GFP) and siDNAs was carried out at 1:1 ratio with Lipofectamine Plus™ reagent (Life Technologies, GibcoBRL) as described by the manufacturer. 0.5 mg pIND-rev-GFP and 0.5 mg siDNAs and 0.1 mg pCMV-lacZ (for transfection efficiency), formulated into Lipofectamine Plus, were applied per 6-well culture. Cells were incubated overnight and on the following day 5 mM Ponasterone A (Invitrogen) was added to induce expression of pIND-rev-EGFP. Two days post induction the transfected cells were harvested to measure EGFP fluorescence by FACS using a modular flow cytometer (Cytomation, Fl). Transfection efficiencies were normalized using a fluorescent b-galactosidase assay (Diagnostic Chemicals Ltd, CN). Fluorescent microscope imaging was also performed to monitor EGFP expression. For the microscopic visualization, cells were grown on glass coverslips in 24-well plates. Co-transfections were carried out on glass coverslips using 0.25 mg each of rev-EGFP and siRNA expression plasmid DNAs (total 0.5 mg). After 2 days, transfected cells were fixed in 4% PFA for 15 minutes at room temperature and treated with antifading reagent containing DAPI. Images were collected using an Olympus BX50 microscope and a DEI-750 video camera (Optronics) at 40× magnification with exposure time of ⅛ sec. Specific silencing of target genes was confirmed in at least three independent experiments.

Example 4

Northern Blotting

RNA samples were prepared from 293-EcR cells transiently co-transfected with pIND-rev-GFP and siRNAs and subjected to Ponasterone A induction as described above. Total RNA isolation was preformed using the RNA STAT-60 (TEL-TEST "B") according to the manufacturer's instruction. The total RNA was resolved on a 10% acrylamide/8M urea gel for siRNAs or a 1% agarose/formamide gel for the target, and transferred onto Hybond-N$^+$ membrane (Amersham Pharmacia Biotech). The hybridization and wash steps were performed at 37° C. To detect the sense or antisense siRNAs, radiolabeled 21-mer DNA probes were used. Human U6 snRNA and GAPDH mRNA were also probed for as internal standards. To detect the ribozyme targeted against site II of the rev mRNA, a 42-mer probe complementary to the entire ribozyme core and flanking sequences was used (this probe also detects the antisense siRNA oligomer for site II). For characterization of the aberrantly sized 46-nt RNAs, total RNAs from S/AS(I+II) were treated with a mixture of RNAase A and T1 for 30 minutes at 37° C. either with or without preheating at 90° C. for 5 minutes.

For detection of the rev-EGFP mRNA, a 25-mer probe complementary to the EFP mRNA of the rev-GFP fusion protein was used.

Example 5

HIV-1 Antiviral Assay

For determination of anti-HIV-1 activity of the siRNAs, transient assays were performed by cotransfection of siDNAs and infectious HIV-1 proviral DNA, pNL4-3 into 293 cells. Prior to transfection, the cells were grown for 24 hours in six-well plates in 2 ml EMEM supplemented with 10% FBS and 2 mM L-glutamine, and transfected using Lipofectamine Plus™ reagent (Life Technologies, GibcoBRL) as described by the manufacturer. The DNA mixtures consisting of 0.8 µg siDNAs or controls, and 0.2 µg pNL4-3 were formulated into cationic lipids and applied to the cells. After 1, 2, 3 and 4 days, supernatants were collected and analyzed for HIV-1 p24 antigen (Beckman Coulter Corp). The p24 values were calculated with the aid of the Dynatech MR5000 ELISA plate reader (Dynatech Lab Inc). Cell viability was also performed using a Trypan Blue dye exclusion count at 4 days after transfection.

The above demonstrates the invention's utility for, among other things, designing and testing siRNA transcripts for a variety of genetic and therapeutic applications. The invention also is believed to demonstrate for the first time the functional expression of siRNAs in mammalian cells.

The above results also demonstrate the utility of siRNAs as HIV-1 inhibitory agents. By combining several siRNA constructs targeted to different sites in the HIV-1 genome, it should be possible to circumvent genetic resistance of the virus, thereby creating a potent gene therapy approach for the treatment of HIV-1 infection.

The publications and other materials cited herein to illuminate the background of the invention and to provide additional details respecting the practice of the invention are incorporated herein by reference to the same extent as if they were individually indicated to be incorporated by reference.

While the invention has been disclosed by reference to the details of preferred embodiments of the invention, it is to be understood that the disclosure is intended in an illustrative rather than a limiting sense, as it is contemplated that modifications will readily occur to those skilled in the art, within the spirit of the invention and the scope of the appended claims.

REFERENCES

Bernstein, E., Caudy, A. A., Hammond, S. M. & Hannon, G. J. Role for a bidentate ribonuclease in the initiation step of RNA interference. *Nature* 409, 363-366 (2001).

Bertrand, E. et al. The expression cassette determines the functional activity of ribozymes in mammalian cells by controlling their intracellular localization. *Rna* 3, 75-88 (1997).

Caplen, N. J., Parrish, S., Imani, F., Fire, A. & Morgan, R. A. Specific inhibition of gene expression by small double-stranded RNAs in invertebrate and vertebrate systems. *Proc Natl Acad Sci USA* 98, 9742-9747 (2001).

Clemens, J. C. et al. Use of double-stranded RNA interference in *Drosophila* cell lines to dissect signal transduction pathways. *Proc Natl Acad Sci USA* 97, 6499-6503 (2000).

Cogoni, C. & Macino, G. Posttranscriptional gene silencing in Neurospora by a RecQ DNA helicase. *Science* 286, 2342-2344 (1999).

Dalmay, T., Horsefield, R., Braunstein, T. H. & Baulcombe, D. C. SDE3 encodes an RNA helicase required for post-transcriptional gene silencing in *Arabidopsis*. *Embo J* 20, 2069-2078 (2001).

Elbashir, S. M. et al. Duplexes of 21-nucleotide RNAs mediate RNA interference in cultured mammalian cells. *Nature* 411, 494-498 (2001).

Elbashir, S. M., Lendeckel, W. & Tuschl, T. RNA interference is mediated by 21- and 22-nucleotide RNAs. *Genes Dev* 15, 188-200 (2001).

Fire, A. RNA-triggered gene silencing. *Trends Genet* 15, 358-363 (1999).

Fire, A. et al. Potent and specific genetic interference by double-stranded RNA in *Caenorhabditis elegans*. *Nature* 391, 806-811 (1998).

Good, P. D. et al. Expression of small, therapeutic RNAs in human cell nuclei. *Gene Ther* 4, 45-54 (1997).

Hammond, S. M., Bernstein, E., Beach, D. & Hannon, G. J. An RNA-directed nuclease mediates post-transcriptional gene silencing in *Drosophila* cells. *Nature* 404, 293-296 (2000).

Kennerdell, J. R. & Carthew, R. W. Use of dsRNA-mediated genetic interference to demonstrate that frizzled and frizzled 2 act in the wingless pathway. *Cell* 95, 1017-1026 (1998).

Lee, N. S., Bertrand, E. & Rossi, J. mRNA localization signals can enhance the intracellular effectiveness of hammerhead ribozymes. *RNA* 5, 1200-1209 (1999).

Lee, N. S. et al. Functional colocalization of ribozymes and target mRNAs in *Drosophila* oocytes. *Faseb J* 15, 2390-2400 (2001).

Lipardi, C., Wei, Q. & Paterson, B. M. RNAi as Random Degradative PCR. siRNA Primers Convert mRNA into dsRNAs that Are Degraded to Generate New siRNAs. *Cell* 107, 297-307 (2001).

Nykanen, A., Haley, B. & Zamore, P. D. ATP requirements and small interfering RNA structure in the RNA interference pathway. *Cell* 107, 309-321 (2001).

Oelgeschlager, M., Larrain, J., Geissert, D. & De Robertis, E. M. The evolutionarily conserved BMP-binding protein Twisted gastrulation promotes BMP signalling. *Nature* 405, 757-763 (2000).

Scherr, M. & Rossi, J. J. Rapid determination and quantitation of the accessibility to native RNAs by antisense oligodeoxynucleotides in murine cell extracts. *Nucleic Acids Res* 26, 5079-5085 (1998).

Scherr, M. et al. Detection of Antisense and Ribozyme Accessible Sites on Native mRNAs: Application to NCOA3 mRNA. *Mol Ther* 4, 454-460 (2001).

Sharp, P. A. RNA interference—2001. *Genes Dev* 15, 485-490 (2001).

Sijen, T. et al. On the Role of RNA Amplification in dsRNA-Triggered Gene Silencing. *Cell* 107, 465-476 (2001).

Smardon, A. et al. EGO-1 is related to RNA-directed RNA polymerase and functions in germ-line development and RNA interference in *C. elegans*. *Curr Biol* 10, 169-178 (2000).

Svoboda, P., Stein, P., Hayashi, H. & Schultz, R. M. Selective reduction of dormant maternal mRNAs in mouse oocytes by RNA interference. *Development* 127, 4147-4156 (2000).

Ui-Tei, K., Zenno, S., Miyata, Y. & Saigo, K. Sensitive assay of RNA interference in *Drosophila* and Chinese hamster cultured cells using firefly luciferase gene as target. *FEBS Lett* 479, 79-82 (2000).

Wianny, F. & Zemicka-Goetz, M. Specific interference with gene function by double-stranded RNA in early mouse development. *Nat Cell Biol* 2, 70-75 (2000).

What is claimed is:

1. A method for testing the expression and function of a small interfering RNA (siRNA) molecule, comprising:

co-introducing into a mammalian cell (a) one or more vectors comprising (i) a first cassette comprising an RNA pol III promoter operatively linked to a first nucleic acid encoding a sense strand of a double stranded siRNA molecule and (ii) a second cassette comprising an RNA pol III promoter operatively linked to a second nucleic acid encoding an antisense strand of the double stranded siRNA molecule, wherein the first nucleic acid comprises a DNA sequence encoding the sense strand positioned at the first nucleotide of the transcript of the RNA pol III promoter and the second nucleic acid comprises a DNA sequence encoding the antisense strand positioned at the first nucleotide of the transcript of the RNA pol III promoter, wherein the first cassette and the second cassette are in a same vector or are in separate vectors and wherein the double stranded siRNA molecule is specific for a target sequence in a target gene, and (b) a vector comprising the target gene and a suitable second promoter;

growing the mammalian cell under conditions suitable for expression of the nucleic acid sequences and the target gene;

determining if the double stranded siRNA molecule is expressed and if expression of the target gene is reduced, whereby the expression and function of the siRNA molecule is tested.

2. The method of claim 1, wherein the mammalian cell is a human cell.

3. The method of claim 1, wherein the nucleic acid sequences are in separate vectors.

4. The method of claim 1, wherein the nucleic acid sequences are in the same vector.

5. The method of claim 1, wherein at least one of the vectors is a plasmid vector.

6. The method of claim 1, wherein at least one of the vectors is a viral vector.

7. The method of claim 1, wherein the RNA pol III promoter is a mammalian U6 poly III promoter.

* * * * *

SEQUENCE LISTING

```
<160> NUMBER OF SEQ ID NOS: 11

<210> SEQ ID NO 1
<211> LENGTH: 35
<212> TYPE: DNA
<213> ORGANISM: Artificial Sequence
<220> FEATURE:
<223> OTHER INFORMATION: Antisense siDNA

<400> SEQUENCE: 1
gctcttcgtc gctgtctccg cttttttgct ctaga                        35
```

```
<210> SEQ ID NO 2
<211> LENGTH: 35
<212> TYPE: DNA
<213> ORGANISM: Artificial Sequence
<220> FEATURE:
<223> OTHER INFORMATION: Sense siDNA

<400> SEQUENCE: 2
gcggagacag cgacgaagag cttttttgct ctaga                                35

<210> SEQ ID NO 3
<211> LENGTH: 35
<212> TYPE: DNA
<213> ORGANISM: Artificial Sequence
<220> FEATURE:
<223> OTHER INFORMATION: Antisense siDNA

<400> SEQUENCE: 3
ggtagctgaa gaggcacagg cttttttgct ctaga                                35

<210> SEQ ID NO 4
<211> LENGTH: 35
<212> TYPE: DNA
<213> ORGANISM: Artificial Sequence
<220> FEATURE:
<223> OTHER INFORMATION: Sense siDNA

<400> SEQUENCE: 4
gcctgtgcct cttcagctac cttttttgct ctaga                                35

<210> SEQ ID NO 5
<211> LENGTH: 23
<212> TYPE: RNA
<213> ORGANISM: Artificial Sequence
<220> FEATURE:
<223> OTHER INFORMATION: Sense siRNA

<400> SEQUENCE: 5
gcggagacag cgacgaagag cuu                                             23

<210> SEQ ID NO 6
<211> LENGTH: 23
<212> TYPE: RNA
<213> ORGANISM: Artificial Sequence
<220> FEATURE:
<223> OTHER INFORMATION: Antisense siRNA

<400> SEQUENCE: 6
gcucuucguc gcugucuccg cuu                                             23

<210> SEQ ID NO 7
<211> LENGTH: 23
<212> TYPE: RNA
<213> ORGANISM: Artificial Sequence
<220> FEATURE:
<223> OTHER INFORMATION: Sense siRNA

<400> SEQUENCE: 7
gccugugccu cuucagcuac cuu                                             23

<210> SEQ ID NO 8
<211> LENGTH: 23
<212> TYPE: RNA
<213> ORGANISM: Artificial Sequence
<220> FEATURE:
```

```
<223> OTHER INFORMATION: Antisense siRNA

<400> SEQUENCE: 8
gguagcugaa gaggcacagg cuu                                              23

<210> SEQ ID NO 9
<211> LENGTH: 26
<212> TYPE: RNA
<213> ORGANISM: Artificial Sequence
<220> FEATURE:
<223> OTHER INFORMATION: Termination sequence

<400> SEQUENCE: 9
ucuagagcgg acuucggucc gcuuuu                                           26

<210> SEQ ID NO 10
<211> LENGTH: 21
<212> TYPE: DNA
<213> ORGANISM: Artificial Sequence
<220> FEATURE:
<223> OTHER INFORMATION: siRNA target site

<400> SEQUENCE: 10
gcctgtgcct cttcagctac c                                                21

<210> SEQ ID NO 11
<211> LENGTH: 21
<212> TYPE: DNA
<213> ORGANISM: Artificial Sequence
<220> FEATURE:
<223> OTHER INFORMATION: siRNA target site

<400> SEQUENCE: 11
gcggagacag cgacgaagag c                                                21
```